United States Patent [19]
Pentoney, Jr. et al.

[11] Patent Number: 5,635,050
[45] Date of Patent: Jun. 3, 1997

[54] ELECTROPHORETIC SYSTEM INCLUDING MEANS FOR REPLACING SEPARATION MEDIUM

[75] Inventors: Stephen L. Pentoney, Jr., Yorba Linda; Brian D. Peterson, Ontario; James C. Osborne, Orange; Charles A. Keenan, Irvine, all of Calif.

[73] Assignee: Beckman Instruments, Inc., Fullerton, Calif.

[21] Appl. No.: 518,285

[22] Filed: Aug. 23, 1995

[51] Int. Cl.⁶ .................................................. G01N 27/26
[52] U.S. Cl. ....................... 204/605; 204/455; 204/453; 204/604
[58] Field of Search .................... 204/299 R, 180.1, 204/182.8, 455, 453, 604, 605

[56] References Cited

U.S. PATENT DOCUMENTS

| | | | |
|---|---|---|---|
| 5,037,523 | 8/1991 | Weinberger et al. | 204/299 R |
| 5,332,481 | 7/1994 | Guttman | 204/455 |
| 5,427,729 | 6/1995 | Dubrow | 264/232 |

OTHER PUBLICATIONS

"Pressure Refilled Polyacrylamide Columns for the Separation of Oligonucleotides by Capillary Electrophoresis," by Jan Sudor, *Electrophoresis*, 1991, 12, 1056–1058.

*Primary Examiner*—Kathryn L. Gorgos
*Assistant Examiner*—Alex Noguerola
*Attorney, Agent, or Firm*—William H. May; Janis C. Henry

[57] ABSTRACT

A gel pump operated by a stepper motor may be used to deliver fresh gel to one or more capillaries through one or more manifolds and valves. By controlling the valves, fresh gel delivered by the pump will replace the old gel in the capillaries for an automated gel replacement system. In a different setting of the valves, the manifolds may be purged of the old gel prior to delivery of fresh gel to the capillaries. The gel delivery system may also be combined with an electrophoresis system so that sealing connection capable of withstanding high pressure adequate for gel injection need not be frequently broken when the gel is to be replaced. Manifold/reflector assembly is advantageously used in the system that facilitates electrical circuit for electrophoresis and for gel replacement.

18 Claims, 7 Drawing Sheets

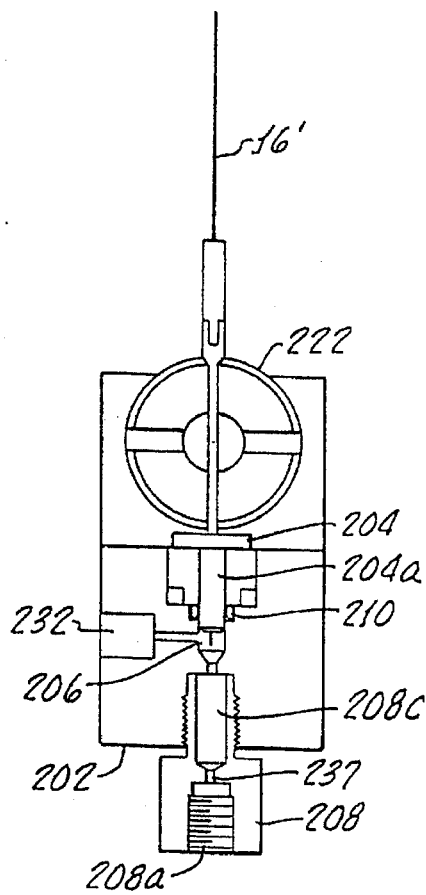
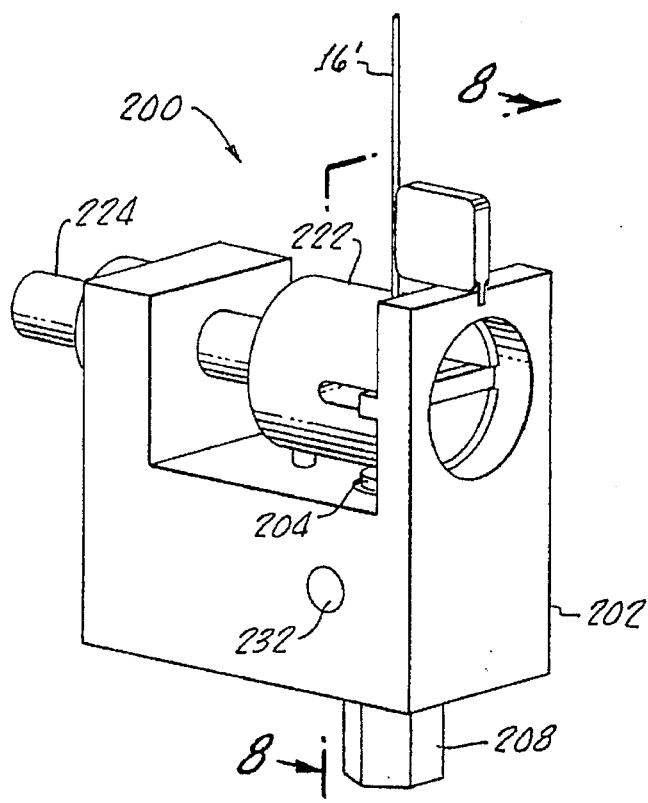
FIG. 7.
FIG. 8.
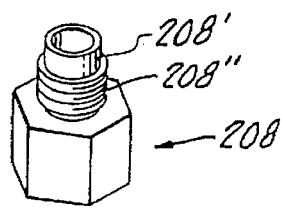
FIG. 9A.
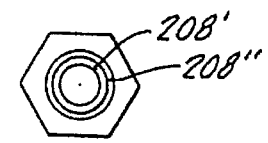
FIG. 9B.
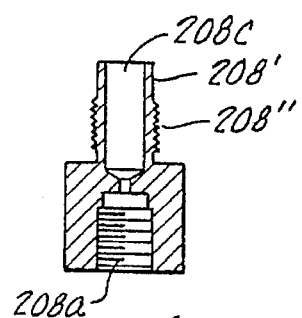
FIG. 9C.

ELECTROPHORETIC SYSTEM INCLUDING MEANS FOR REPLACING SEPARATION MEDIUM

BACKGROUND OF THE INVENTION

This invention relates in general to capillary electrophoresis and, in particular, to a capillary electrophoretic system with means for replacing separation medium in a capillary.

High resolution separation of complex mixtures of biomolecules by capillary electrophoresis often requires the use of highly viscous separation media. For example, polyacrylamide gels in the 4–15 percentage T range (either cross-linked or linear) are currently selected to size-separate the products of Sanger-Coulson DNA sequencing reactions. The use of "fixed" polyacrylamide gels which are polymerized within the capillary and are chemically bound (either covalently or by ionic linkage) to the capillary inner walls has been reported. Although impressive resolution has been demonstrated using fixed gels, the use-life of this type of gel is highly variable and is typically quite short.

An alternative to the fixed gel format is described in "Pressure Refilled Polyacrylamide Columns for the Separation of Oligonucleotides by Capillary Electrophoresis," by Sudor, J. et al., *Electrophoresis*, 1991, 12, 1056–1058. In this approach, the polyacrylamide gel is first polymerized in a syringe and is then driven under high pressure into a wall coated capillary tube. The gel matrix may be replaced under each separation and the column use-life is then determined by the stability of the wall coating rather than by the stability of the fixed gel matrix. The gel is driven by high pressure, such as by hand pressurizing a small volume syringe. Connection of the syringe to the capillary tube was made using either a Teflon sheath or a custom-made tapered glass syringe as described by Sudor et al. The connection was made by hand and had to be made and broken once for each gel replacement. The capillary tube is effectively removed from the electrophoresis circuit during the resealing process.

The replaceable gel currently being produced and used requires 700–1,300 psi pressure to be driven through the capillary tubes with internal diameters of 75–100 microns in a 5–15 minute refill period. This pressure range is far above that which is compatible with easily made and broken seals such as that usually used in capillary electrophoretic systems. Because of this and other factors described above, it is difficult to automate the gel replacement process using conventional or other electrophoretic systems that have been proposed. It is therefore desirable to provide an improved electrophoretic system which avoids the above drawbacks.

SUMMARY OF THE INVENTION

A first aspect of the invention is directed towards an apparatus for delivering a viscous separation medium to one or more capillaries, comprising conduit means for supplying viscous separation medium to a plurality of capillaries, a pump delivering new viscous separation medium, and valve means for controlling the delivery of new viscous separation medium by the pump so that in a first setting of the valve means, the delivery of new viscous separation medium clears the conduit means of old viscous separation medium, and in a second setting of the valve means, the delivery of new viscous separation medium clears old viscous separation medium from and delivers new viscous separation medium to said one or more capillaries.

Another aspect of the invention is directed towards a method for delivering a viscous separation medium to one or more capillaries employing conduit means for supplying viscous separation medium to said one or more capillaries, comprising the steps of delivering new viscous separation medium to displace old viscous separation medium in the conduit means, and delivering new viscous separation medium to said one or more capillaries through said conduit means.

Another aspect of the invention is directed towards an apparatus for electrophoretic separation, comprising medium conduit means; at least one separation capillary having an inlet and an outlet; and control means connecting the outlet of the at least one capillary to the medium conduit means, so that viscous separation medium is injectable from the medium conduit means to the at least one capillary to displace old viscous separation medium in the at least one capillary, and application of an electrical potential across the at least one capillary inlet and the medium conduit means will cause electrophoretic separation of a sample in the at least one capillary.

Yet another aspect of the invention is directed towards a method for electrophoretic separation, comprising the steps of sealingly connecting an outlet of at least one separation capillary having an outlet to medium conduit means to form sealed connections there between so that a predetermined pressure greater than atmospheric pressure can be maintained in the at least one capillary; injecting viscous separation medium into the at least one capillary to purge the at least one capillary of old viscous separation medium, if any, in the at least one capillary by means of the medium conduit means; and applying an electrical field in the at least one capillary to separate any samples present in the at least one capillary. The injecting and applying steps are performed without breaking the sealed connections.

One more aspect of the invention is directed towards an apparatus for use in an electrophoretic device, comprising a housing defining a chamber therein for housing an end of at least one capillary, a first conduit to said chamber for passage of said at least one capillary, and at least an additional conduit for passage of an electrode means and for injection of viscous separation medium into the chamber in order to displace old viscous separation medium, if any, in the at least one capillary.

One additional aspect of the invention is directed towards a method for electrophoretic separation, comprising the steps of providing a housing defining a chamber therein for housing an end of at least one capillary, a first conduit to said chamber for passage of said at least one capillary, and at least an additional conduit for passage of an electrode and for injection of viscous separation medium into the chamber in order to displace old viscous separation medium, if any, in the at least one capillary. The method further comprises the steps of injecting viscous separation medium into the chamber to purge the chamber and the at least one capillary to purge the chamber and the at least one capillary of old viscous separation medium, if any, by means of the at least one additional conduit; connecting an electrode to said at least one additional conduit; and applying an electrical potential between the electrode and the viscous separation medium in the at least one capillary to cause separation of any sample in the at least one capillary.

In the preferred embodiment of the aspects of the invention above, the viscous separation medium is a gel. The preferred embodiment of the invention is described below by reference to gel as the separation medium.

BRIEF DESCRIPTION OF THE DRAWINGS

FIG. 7 is a perspective view of the assembly of FIG. 6 from another angle from the back.

FIG. 8 is a cross-sectional view of the assembly of FIGS. 6 and 7 taken along the line 8—8 in FIG. 7.

FIG. 9A is a perspective view of a electrode fitting portion of FIGS. 6–8. FIG. 9B is a top view of the fitting of FIG. 9A and FIG. 9C is a cross-sectional view of the electrode fitting of FIG. 9A along the line 9C–9C in FIG. 9A.

For convenience in description, identical components in this application are labeled by the same alpha numeric labels.

DETAILED DESCRIPTION OF THE PREFERRED EMBODIMENT

Figure 1:
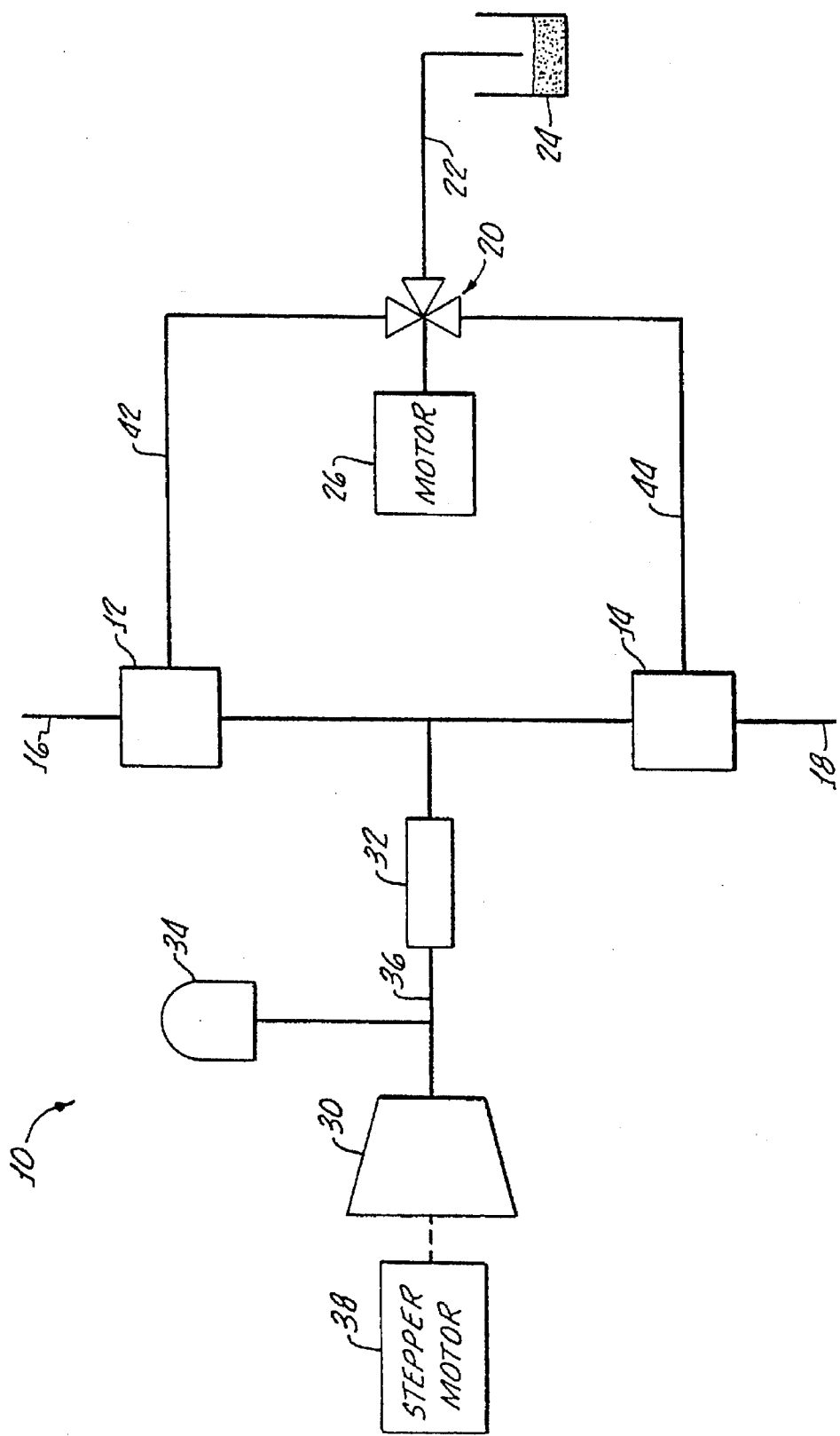
FIG. 1 is a schematic view of a system equipped with a device for replacing gel medium in the capillaries by new gel to illustrate a first embodiment of the invention.

FIG. 1 is a schematic view of a system for displacing old gel in the capillaries with new gel to illustrate the invention. System 10 of FIG. 1 includes two manifolds 12 and 14. Manifold 12 is used for injecting new gel into one or more capillaries 16 to displace the old gel in these capillaries by new gel. Similarly, manifold 14 is used for injecting new gel into one or more capillaries 18 to displace the old gel therein. Manifolds 12 and 14 are connected by gel delivery lines to a three-way valve 20. Valve 20 is in turn connected to a waste line 22 so that the gel waste passing through the valve and line 22 may be deposited into a gel waste container 24. Valve 20 is controlled by motor 26 in order to connect one of the two manifolds 12 and 14 with waste line 22. Manifolds 12 and 14 are connected by delivery lines to a gel pump 30 through a back press regulator 32. A pressure sensor 34 senses the pressure in the delivery line 36 connecting the pump and the regulator.

Manifolds 12 and 14 are used in each filling process for displacing the gel in the one or more capillaries 16, 18. Therefore, when system 10 is used to deliver new gel to the capillaries 16, 18, the manifolds may contain gel which was left over from the prior delivering process so that it is desirable to purge the manifolds of the old gel. To purge manifold 12, motor 26 operates valve 20 to connect manifold 12 to waste line 22. Pump 30 is then operated by the stepper motor 38 to deliver a predetermined amount of gel in order to purge manifold 12 of the old gel therein. This would then fill manifold 12 with new gel and would greatly reduce the chances that the old gel originally present in manifold 12 would contaminate the new gel delivered by the pump to the one or more capillaries 16. The waste line 42 connecting manifold 12 and valve 20 as well as waste line 22 are much larger in dimensions than the inner diameters of the one or more capillaries 16, so that most of the gel delivered by the pump would flow through manifold 12, line 42, valve 20, and line 22 to container 24, instead of to the one or more capillaries 16.

After the old gel in manifold 12 has been purged as described above, motor 26 is used to control valve 20 so as to disconnect line 22 from line 42 and instead connect it to line 44 leading to manifold 14. Pump 30 again delivers new gel in order to purge manifold 14 of the old gel through line 44, valve 20 and line 22. After both manifolds have been purged of the old gel, motor 26 is used to disconnect line 22 from lines 42 and 44. Pump 30 is then controlled by stepper motor 38 to deliver gel to line 36. During the delivery, the pressure in line 36 is sensed by pressure sensor 34 so that a high pressure in line 36 (such as 1200 psi) is maintained during the delivery. In one embodiment, approximately three capillary volumes of gel is delivered through each of the capillaries 16, 18. Motor 26 then causes valve 20 to connect lines 42, 24 to line 22 and pump 30 may then be reversed to depressurize the system. The back pressure regulator 32 closes when the high pressure in the manifolds, 12, 14, the capillaries, lines 42, 44, 22 and lines connecting the regulator to manifolds 12, 14 are released and vented to the atmosphere.

While two manifolds 12 and 14 are shown in FIG. 1, it will be understood that fewer or more manifolds may be used for delivering gel to displace old gel in fewer or more than two capillaries or two groups of capillaries. All such variations are within the scope of the invention. System 10 is advantageous in that it completely automates the process of filling the capillaries with new gel. No gas pressure is used and the system lends itself to microprocessor automated control. The system permits delivery of a pre-set volume of gel at a pre-set head pressure.

In system 10 described above, after the capillaries 16, 18 receive new gel, these capillaries are then ready to be used for electrophoretic separation of samples. After a number of electrophoretic runs, the gel in such capillaries would again need to be replaced and the above-described process would then need to be repeated. As noted above the gel replacement process requires gel pressurized at 400 psi or above be driven to the capillary tubes. This pressure range is far above that normally compatible with easily made and broken seals such as those used in normal capillary electrophoresis systems. If the capillary tubes must be effectively removed from the electrophoresis circuit each time the gel is replaced, this means that seals able to withstand high pressures must be made and broken frequently and the process of gel replacement would be cumbersome. It is therefore desirable to provide an electrophoretic system where the gel replacement process can be made without the need to frequently make and break the high pressure seal to the capillary. Such a system is described below in reference to FIGS. 2–5 below.

Figure 2:
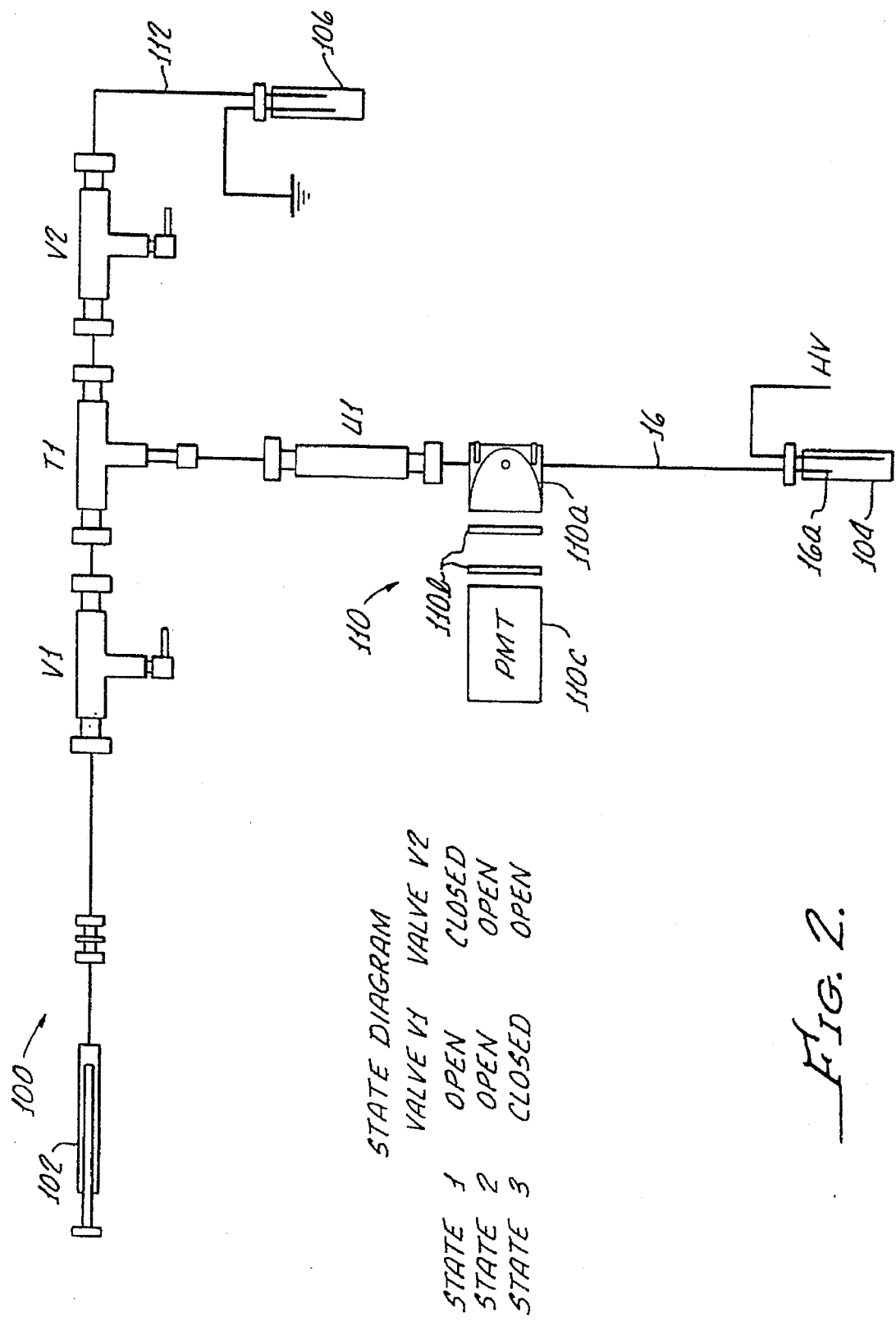
FIG. 2 is a schematic view of an electrophoretic system employing a device to replace old gel in the capillary by new gel and to perform electrophoresis to illustrate a second embodiment of the invention.

FIG. 2 is a schematic view of an electrophoretic system 100 which permits gel in the one or more separation capillaries 16 to be replaced without having to frequently make and break a high pressure seal to the capillary adequate for the gel replacement process. As shown in FIG. 2, fresh gel may be injected into the one or more capillaries 16 through their outlet ends by means of a gel-filled syringe 102. The outlet end or ends (not shown) of the one or more capillaries 16 may be connected to and sealed in a chamber in housing U1. As fresh gel is injected into the one or more capillaries 16, the stale or old gel in the one or more capillaries would emerge through the inlet end or ends into the inlet buffer reservoir 104. After the one or more capillaries 16 have been purged of old gel and filled with fresh gel, one or more samples to be separated may be introduced into the one or more capillaries through the one or more inlet ends 16a. The outlet end or ends of the one or more capillaries 16 are connected electrically to an output buffer 106 by means of an electrolyte in a manner described below. A separation electrical potential is then applied across the inlet and outlet buffer reservoirs 104, 106 causing the one or more samples injected to be separated by electrophoresis as the sample components migrate from the one or more inlet ends 16a towards the one or more outlet ends. These separated sample components are detected by means of detector 110 which includes a parabolic reflector 110a, filters 110b, and photomultiplier tube 110c. A laser is used to induce fluorescence of tagged samples and such fluorescence is then detected by means of reflector 110a which collects the light and filters 110b filters the emission light collected and passes it onto the photomultiplier tube 110c for detection in a manner known to those skilled in the art. For simplicity, the laser source is not shown in FIG. 2.

The installation of system 100 is as follows. First, a high pressure seal is made directly to the one or more capillaries 16 using a non-conductive high pressure compression fitting. This seal remains in place for the use-life of the capillary column which is determined by the capillary wall coating material and not by the life of the gel. This high pressure seal is made to the outlet end or ends of the one or more capillaries 16 after the detector 110 to eliminate volume constraints. Since the valving system for gel replacement is connected to the outlet end of the capillary, the sample components do not reach such valving system until after they have been detected by detector 110. Hence, no electrophoretic resolution losses are encountered regardless of the volumes of the valving system and the associated connecting tubing. This then leaves the inlet end or ends 16a available for interfacing with low volume samples on an automatic sample injector (not shown).

The control of the valving system for gel replacement and for electrophoresis will now be described. In state one, system 100 is configured for gel replacement. In state one, valve V1 is open and valve V2 is closed. The fresh gel from syringe 102 therefore passes through valve V1, the chamber in T-connector T1, the chamber in connector U1 and from there into the outlet end or ends of the one or more capillaries 16. As noted above, displaced old gel from the one or more capillaries would exit into buffer 104.

After the one or more capillaries have been purged, valve V2 is opened and valve V1 remains open, in state two. In state two, system 100 is configured for pressure relief and purging of the valving system and gel lines. Thus, when valve V2 is open, the high pressure required for the gel replacement process is relieved through the valve V2 and tubing 112. Fresh gel delivered by syringe 102 then purges the chamber in T-connector T1 and valve V2 as well as tubing 112 of the old gel.

In state three, device 100 is configured for electrophoresis. During this state, valve V1 is closed and valve V2 remains open. A high electrical potential is applied by a power supply (not shown) between the two buffers 104, 106. The electrical circuit is completed through the buffers 104, 106 and the gel medium in the one or more capillaries 16, and the gel medium in the chambers in connector U1, T-connector T1, valve V2, and in tubing 112. The electrophoretic current therefore passes from the high voltage electrode at the one or more capillary inlets 16a, buffer 104, through the capillary column(s) and finally through the valving system to the electrically grounded buffer 106. It will be noted that electrical contact to the high voltage power supply via metal electrodes is made externally and in buffer reservoirs to narrow bore tubing and/or passageways in order to avoid current failures associated with trapping of gas as generated at the metal electrode surfaces. The high pressure seal and gel replacement valving system connected to the outlet(s) of the one or more capillaries are placed in a grounded state of the electrophoresis circuit in order to avoid arcing problems.

The gel-filled syringe 102 contains the prepolymerized polyacrylamide of a formulation suitable for DNA sequencing, for example. In research platforms, the syringe is simply mounted in a vice equipped with a force gauge. In commercial systems, syringe 102 is preferably replaced by a programmable gel delivery system such as that shown in FIG. 1. In FIG. 2, the syringe is coupled to narrow bore (0.015–0.020 inches internal diameter) FEP or other type tubing using a compression type union. In the preferred embodiment, syringe 102 is replaced by pump 30, regulator 32, sensor 34, conduit 36 and motor 38 of FIG. 1, where regulator 32 is connected by a gel delivery line to valve V1. Pump 30, regulator 32, sensor 34, conduit 36 and motor 38, when used to replace syringe 102, perform the same functions as those described above in reference to FIG. 1. Thus, when pump 30 is delivering gel to the valving system and the one or more capillaries, sensor 34 is used to sense the pressure in conduit 36. Regulator 32 disconnects the pump 30 and conduit 36 from the valving system downstream from and connected to regulator 32 when the system is vented to atmospheric pressure and also when the system is employed to perform electrophoresis as described above. This prevents gel from being injected into the capillaries or the remaining portion of the electrophoretic circuit path between buffers 104, 106 to disturb the electrophoresis process.

It is noted that samples injected may migrate into the gel in the valving system during electrophoresis. Thus migrated components left in the valving system from prior electrophoretic runs may contaminate the sample in the current run. However, since the valving and tubing systems downstream from the outlet or outlets of the one or more capillaries in the electrophoresis migration direction are much larger in dimensions compared to the cross-sectional dimensions of the one or more capillaries, the electric field in the gel medium inside the valving system as well as associated tubing are much lower than that inside the one or more capillaries. Hence, migration distances are expected to be very small in the valving system. This problem is further addressed in the embodiment illustrated in FIGS. 3 and 4.

Figure 3:
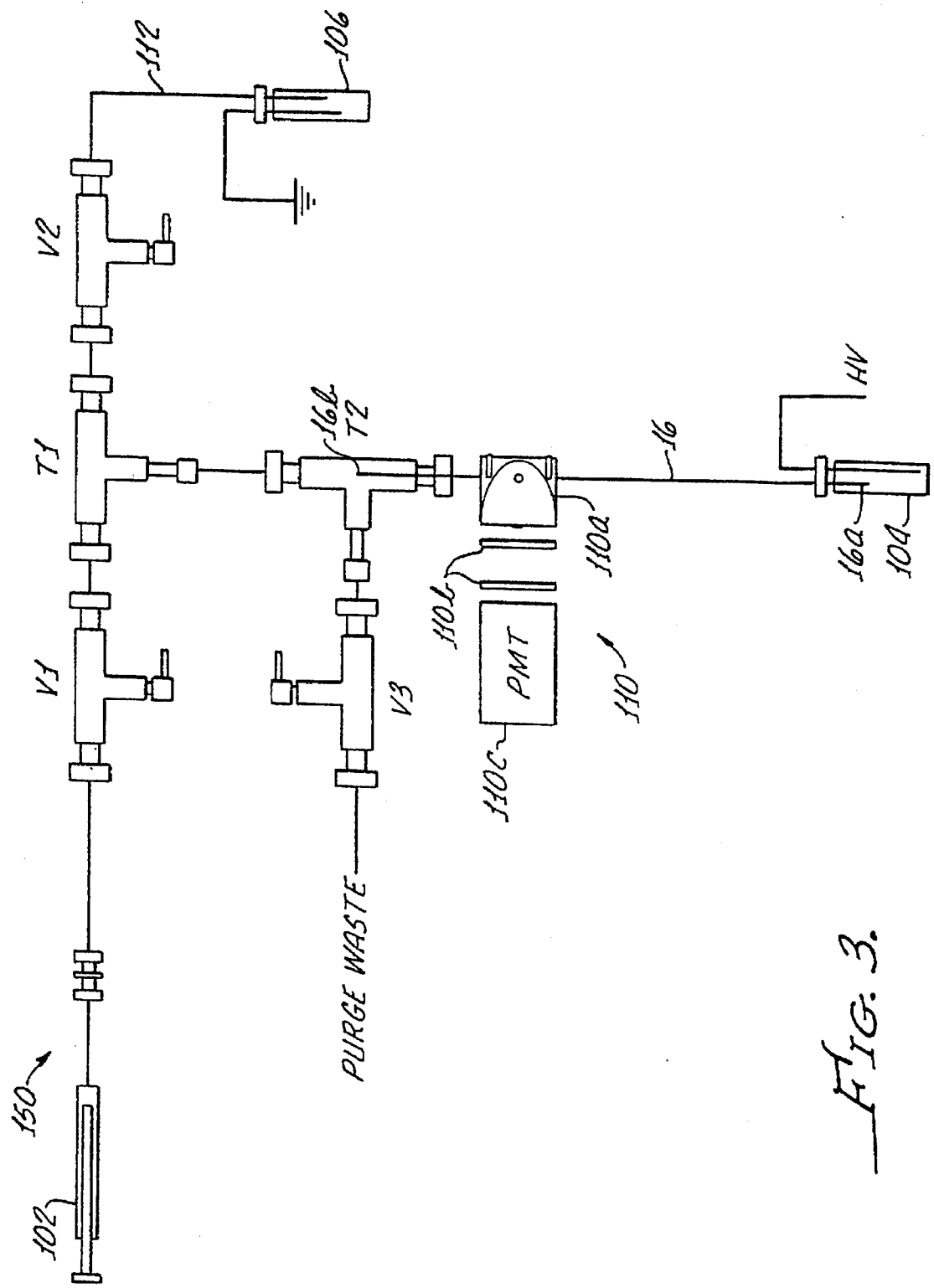
FIGS. 3 and 4 are schematic views of electrophoretic systems which are modified versions of the system of FIG. 2 to illustrate a third and fourth embodiments of the invention.

FIG. 3 is a schematic view of an electrophoretic system with means for replacing gel in one or more separation capillaries with fresh gel as in FIG. 2 and further provided with means for purging the valve system of any gas bubbles as well as any sample components from previous electrophoretic runs. System 150 differs from system 100 of FIG. 2 in that connector U1 is replaced by a T-shaped T-connector T2 having a chamber t2 therein for housing the outlet end or ends 16b of the one or more capillaries 16 and connected to valve V3 through which waste gel can be disposed of. The old gel in T-connector T1 and valve V2 and tubing 112 is first purged before new gel is delivered to the capillaries. To accomplish this result, valve V3 is closed, and the other two valves are open so that the fresh gel delivered by syringe 102 will purge the chambers in V1, T1, V2 of the system 150. Then in order to purge the valving system between T-connector T1 and the capillary tip or tips 16b to eliminate any trapped air or other gas forced into this system from the pumping mechanism, valve V2 is closed and the other two valves are open so that the fresh gel delivered by syringe 102 will purge such part of the valving system through valve V3. Thus when valve V1 is open and valves V2, V3 are closed, the fresh gel delivered by syringe 102 (or pump 30, regulator 32, sensor 34, conduit 36, motor 38) is delivered to the one or more capillaries 16 through the outlet ends to displace the old or stale gel therein through the inlet end or ends 16a and into buffer reservoir 104. To relieve the pressure required during the gel replacement process, all three valves are opened.

Figure 4:
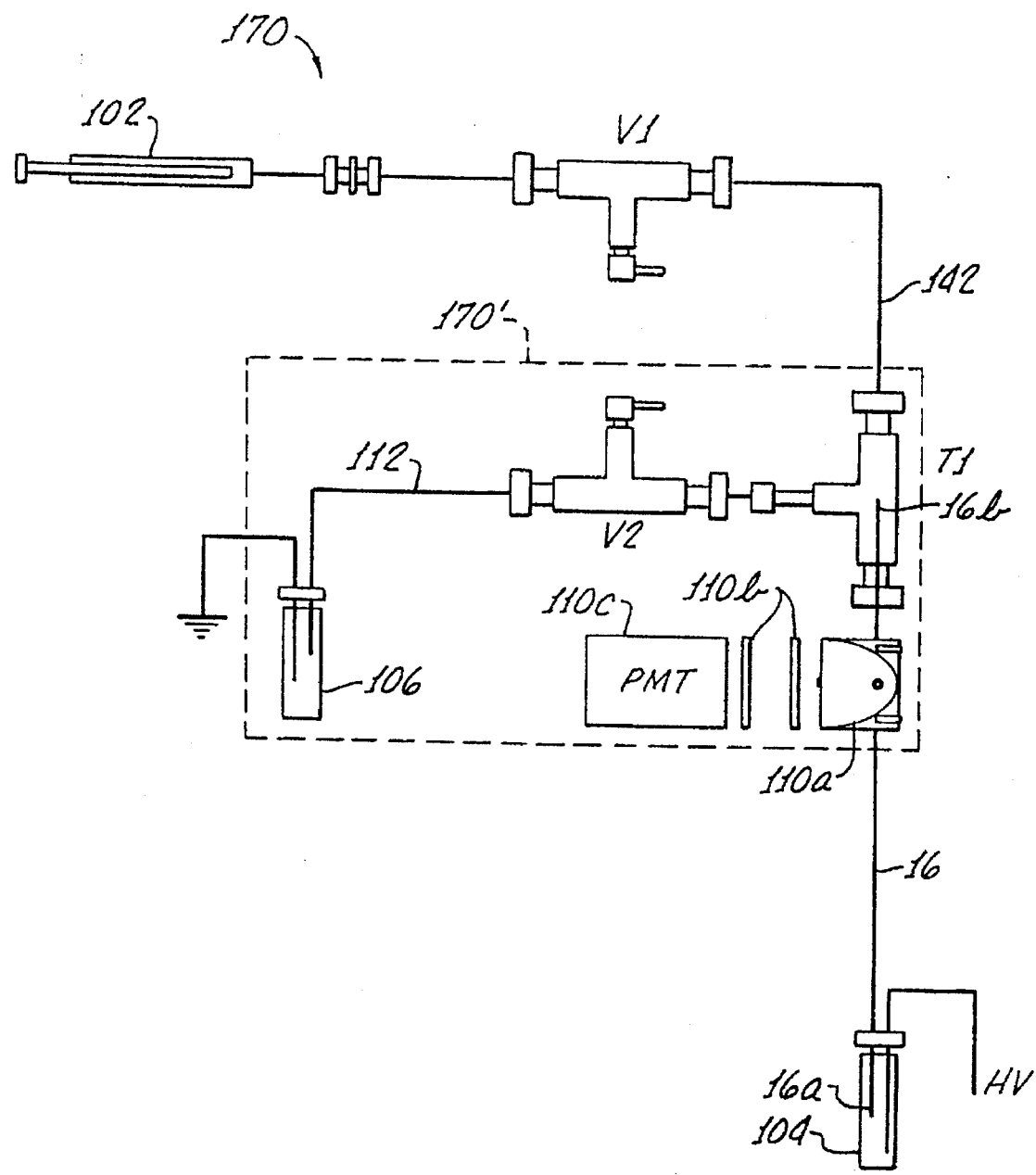

FIG. 4 is a schematic view of an electrophoretic system similar in construction to system 150 of FIG. 3 except that T-connector T2 and valve V3 have been eliminated by rearranging the connections between the capillary and valve V2 to T-connector T1 in a manner so that the outlet end or ends 16b of the one or more capillaries 16 extend into and is housed by chamber t1 in T-connector T1 as shown in FIG. 4. In order to purge chamber t1, valve V2 and tubing 112 of any trapped air or gas, both valves V1, V2 are open when gel is delivered. As before since the separation capillary or capillaries have much smaller internal diameters compared to the valving system, when both valves are open, fresh gel delivered will have the effect of purging chamber t1 and valve V2 and tubing 112 of old gel and any trapped air or gas therein. The purging process described above in reference to FIGS. 3 and 4 also has the effect of purging the gel in the valving systems of any sample components that have migrated into the valving system from prior electrophoretic runs. Then, to replace the gel in the one or more capillaries 16, valve V1 is open and valve V2 is closed when gel is delivered by syringe 102 (or pump 30, regulator 32, sensor 34, conduit 36, motor 38).

Figure 5:
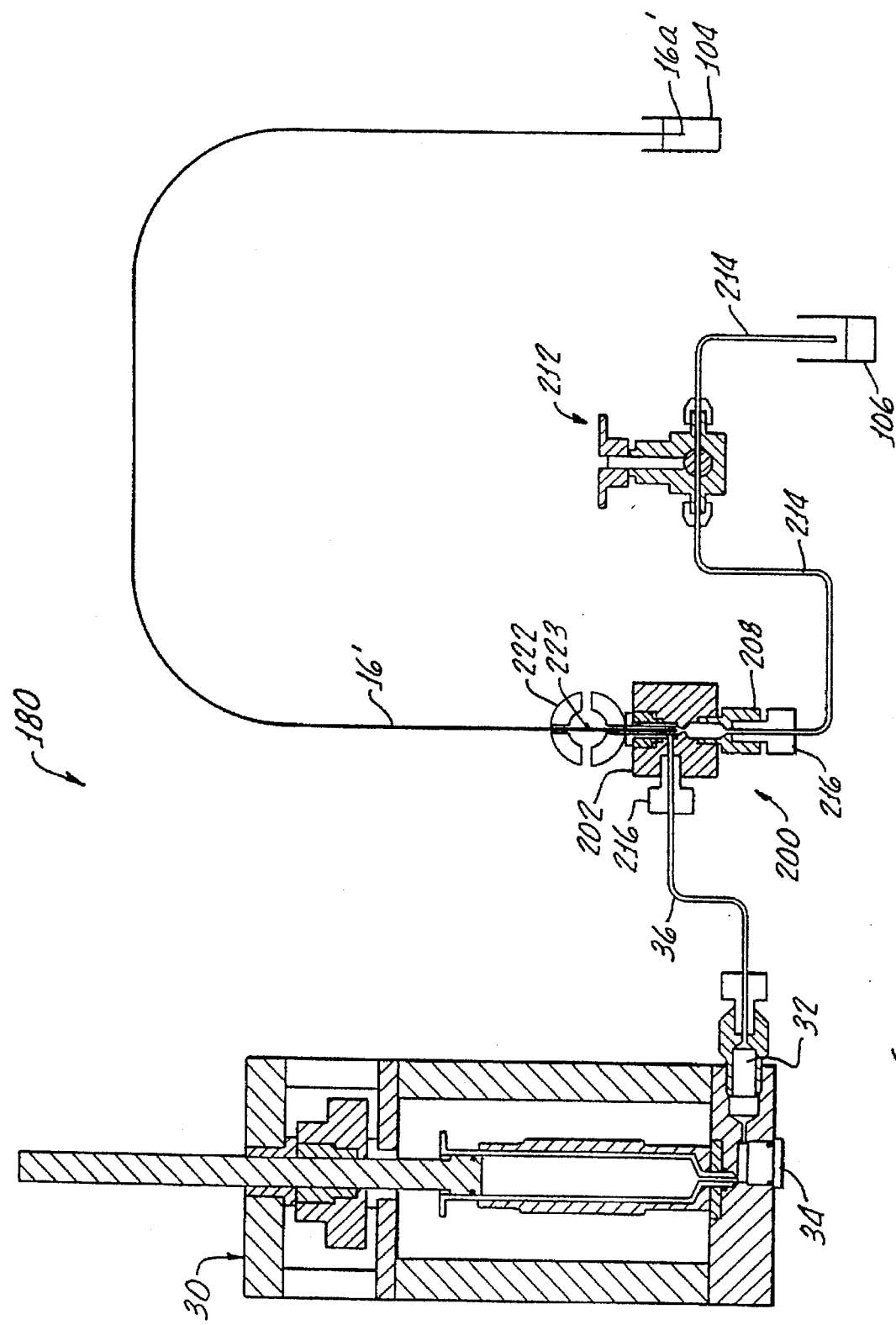
FIG. 5 is a schematic view of an electrophoretic system having a manifold/reflector assembly portion to illustrate the preferred embodiment of the invention.

FIG. 5 is a schematic view of an electrophoretic system 180 which operates in a similar manner as systems 150, 170 of FIGS. 1–4. As in the case of system 10 of FIG. 1, in system 180, gel is delivered by means of a gel pump 30 where the pressure of the gel delivered is sensed by pressure sensor 34 and a back regulator 32 isolates pump 30 from line 36 when the portion of the system 180 downstream from line 36 is vented to the atmosphere. Line 36 is connected to manifold 200 by means of a nut 216 having grooves complementary to those of a hole in the manifold so that the nut can be screwed in the hole. Line 36 is threaded through a hole in nut 216 and is sealingly held therein by means of non-conductive high pressure compression fitting. In this manner, high pressure gel can be delivered by pump 30 through line 36 to a chamber within manifold 200.

The outlet end(s) of one or more capillaries 16' are enclosed within the chamber in the manifold 200 so that the gel delivered through line 36 can be used to displace old gel in the capillary array 16' into reservoir 104. As described in more detail below, electrode fitting 208 can be screwed into a threaded hole in the manifold 200, where the electrode fitting can be used as one terminal for applying electrical potential. Hence, if an electrical potential is applied between buffer 104 and electrode fitting 208, the electric field present in the capillary array 16' may be used for electrophoretic separation.

Thus, as before, one or more samples may be introduced into the capillaries in array 16' through their ends 16'a. The separated components may be detected with the aid of reflector 222 and a detector (not shown) in detection window 223. Some of the separated components may migrate into the chamber within manifold 200. To prevent the components from previous runs in such chamber from contaminating the gel to be delivered to the array 16', it will be desirable to purge the chamber within manifold 200 of the old gel prior to another electrophoretic run. Electrode fitting 208 has a hole therein through which the old gel in the chamber in manifold 200 may be purged. For this purpose, another gel line 214 for disposal of waste gel is connected to such hole in the electrode fitting by means of another nut 216 which is screwed into a complementary hole within electrode fitting 208. Line 214 passes through a hole in nut 216 and is sealingly attached thereto by non-conductive high pressure compression fitting. A waste valve 212 controls line 214. Therefore, when the old gel within the chamber in manifold 200 is to be purged, waste valve 212 is opened and pump 30 delivers new gel to the chamber in order to purge it of the old gel, which exits through line 214 to waste reservoir 106. After the purging process, valve 212 is closed so that array 16' may then be purged by means of new gel from pump 30 as in systems described above and the system is then ready for another electrophoretic run.

Figure 6:
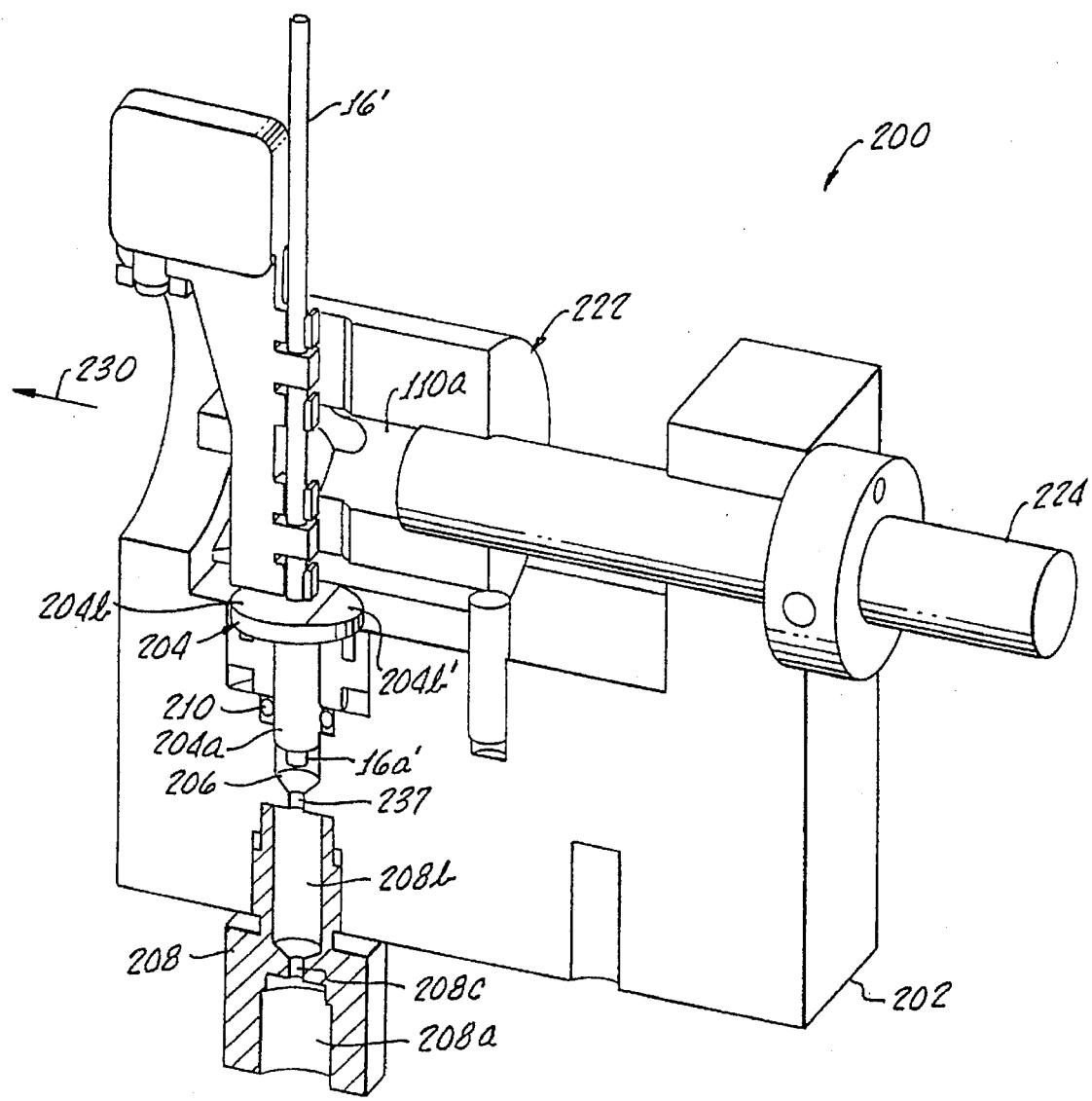
FIG. 6 is a perspective view of the manifold/reflector assembly portion of the electrophoretic system of FIG. 5 with portions cut away to illustrate the preferred embodiment of the assembly.

FIG. 6 is a perspective view of a portion 200 of the electrophoretic system 180 of FIG. 5 including the manifold 202 with portions cut away to illustrate the preferred embodiment of the invention. In reference to FIGS. 4 snd 6, system portion 200 may also be used to replace portion 170' in FIG. 4. To simplify the drawing, the lenses 110b and photomultiplier tube 110c of FIG. 4 are not shown in FIG. 6, which shows only the parabolic mirror 110a. The connection between gel inlet line (similar to line 142 of FIG. 4) and the portion 200 also is not shown in FIG. 6; such connection is illustrated in FIGS. 7 and 8. System portion 200 includes a manifold 202, a portion of which has been cut away to reveal the plurality of capillaries 16', parabolic mirror 110a, array holder 204, chamber 206, and electrode fitting 208. The array of capillaries 16 pass through and are held in position by an array holder 204 so that the ends 16a' remain in chamber 206. Array holder 204 has a cylindrical portion 204a which fits snugly into chamber 206 and O-ring 210 provides a sealing connection between the array holder and the chamber wall of chamber 206. Such sealing connection can withstand the required 5 pressure of over 400 psi for the gel replacement process described above. Parabolic mirror 110a is mounted onto an annular member 222 which may slide along guide 224. To assemble the manifold/reflector assembly portion 200 shown in FIG. 6, cylindrical portion 204a of holder 204 is sealingly connected to the chamber wall of chamber 206 as described above, where the holder 204 holds the array of capillaries 16' with ends 16a' inside the chamber. To lock in the sealing connection, annular member 222 is slid along guide 224 in direction 230 to engage the top surface of array holder 204 thereby locking the array holder in place. The top plate portion 204b has a wedge-shaped portion 204b' facing member 222 to facilitate the sliding engagement with member 222. Since the annular member 222 can only move along direction 230 or in the opposite direction to 230, array holder 204 will be locked in place until annular member 222 is slid in a direction opposite to 230.

Electrical circuit for electrophoresis is completed through the gel medium in the capillaries 16', the gel medium in chamber 206, the gel medium in electrode fitting 208 made of an electrically conductive material such as metal, as well as the fitting acting as an electrode. In this manner, no outlet buffer reservoir is required and the ground connection can be made directly to the electrode fitting. The other ends of capillaries 16' are connected to an inlet buffer reservoir (not shown), similar to reservoir 104 shown in FIG. 4. When the gel in capillaries 16' is to be replaced, fresh gel is injected into chamber 206 through an inlet (not shown) in FIG. 6 but shown in FIGS. 5, 7 and 8 described below. As described above, in order to purge chamber 206 of old gel and any trapped gas and air bubbles, the waste valve 212 is opened, so that the old gel may be purged through fitting 208, line 214, valve 212 and reservoir 106. As shown in FIG. 6, fitting 208 defines two cylindrical holes 208a, 208b connected by a small hole 208c. As shown in FIG. 5, hole 208a is connected to line 214 through which the old gel from chamber 206 may be purged to a waste container 106 in FIG. 5.

FIG. 7 is a perspective view of the system portion 200 of FIG. 6 but from a different angle from the back. FIG. 8 is a cross-sectional view of assembly portion 200 along the line 8—8 in FIG. 7. As shown in FIGS. 7 and 8, fresh gel may be injected by a syringe or pump (not shown) through a valve and line (not shown) to gel inlet 232 for supplying fresh gel to chamber 206.

FIG. 9A is a perspective view of electrode fitting 208. As shown in FIGS. 8 and 9A, portion 208' and 208" fit snugly (by means of complimentary threads) onto corresponding surfaces of a hole in manifold 202 to withstand the over 400 psi pressure. As more clearly shown in FIGS. 5 and 8, a small hole 237 in the manifold 202 connects hole 208a (and line 214 of FIG. 5) through hole 208c to chamber 206. FIG. 9B is a top view of fitting 208 and FIG. 9C is a cross-sectional view of the fitting.

Manifold 202 may be made of a plastic material. In one embodiment, electrode fitting 208 has rounded surfaces to keep current density low. The electrode fitting 208 may be made of low resistance, electrically conductive material.

While the invention has been described above by reference to various embodiments, it will be understood that various changes and modifications may be made without departing from the scope of the invention which is to be defined only by the appended claims.

What is claimed is:

1. An apparatus for electrophoretic separation, comprising:
   medium conduit means having medium inlet means and medium outlet means;
   at least one separation capillary having an inlet and an outlet, said capillary being in sealing medium communication with the medium conduit means, said medium conduit means and the at least one capillary containing an electrically conductive medium;
   means for applying an electrical potential across the inlet of the at least one capillary and the medium conduit means; and
   control means controlling the medium inlet and medium outlet means, so that viscous separation medium is injectable through the medium inlet means of the medium conduit means to the at least one capillary to displace old viscous separation medium in the at least one capillary, and so that application of the electrical potential across the electrically conductive medium between the inlet of the at least one capillary and medium conduit means will cause electrophoretic separation of a sample in the at least one capillary, said injection and application of electrical potential accomplished one after the other without breaking the sealing medium communication between the at least one capillary and the medium conduit means.

2. The apparatus of claim 1, said control means connecting the outlet of the at least one capillary to the medium conduit means, so that when the control means causes the medium inlet means to be open, viscous separation medium is injectable from the medium inlet means to the at least one capillary to displace old viscous separation medium in the at least one capillary, and when the control means causes the medium outlet means to be open, application of an electrical potential across said electrically conductive medium between the inlet of the at least one capillary and the medium outlet means will cause electrophoretic separation of a sample in the at least one capillary.

3. The apparatus of claim 2, said control means including one or more valves and conduits.

4. The apparatus of claim 3, said medium conduit means further comprising a chamber in sealing medium communication/with the outlet of the at least one capillary, said control means comprising:
   a first valve connected between the medium inlet means and the chamber controlling the opening and closing of the medium inlet; and means
   a second valve connected between the medium outlet means and the chamber controlling the opening and closing of the medium outlet means.

5. The apparatus of claim 4, said chamber housing the outlet of the at least one capillary, so that by opening the first and second valves when viscous separation medium is injected into the chamber, the chamber is substantially purged of gas bubbles.

6. The apparatus of claim 1, wherein said applying means includes one or more buffer solutions.

7. The apparatus of claim 1, wherein said applying means includes an electrically conductive fixture or electrode.

8. The apparatus of claim 7, wherein said electrically conductive fixture or electrode is connectable sealingly to the medium outlet means for applying the electrical potential across the at least one capillary inlet and the medium conduit means.

9. The apparatus of claim 1, said control means including a rotary valve.

10. The apparatus of claim 1, further comprising:
    a pump for injecting viscous separation medium; and
    means for connecting the pump to the medium conduit means.

11. The apparatus of claim 10, further comprising a back pressure regulator that disconnects the pump from the connecting means when pressure in the one or more capillaries is vented.

12. The apparatus of claim 10, further comprising a stepper motor for controlling amount of viscous separation medium delivered by the pump to the medium conduit means.

13. The apparatus of claim 10, further comprising a pressure sensor for sensing pressure in the connecting means when viscous separation medium is delivered by the pump to the one or more capillaries.

14. The apparatus of claim 1, wherein said sealing communication can withstand over 400 psi.

15. A method for electrophoretic separation, comprising the steps of:
    sealingly connecting at least one separation capillary to medium conduit means to form sealed connections there between so that a predetermined pressure greater than atmospheric pressure can be maintained in the at least one capillary;
    injecting viscous separation medium into the at least one capillary to purge the at least one capillary of old viscous separation medium, if any, in the at least one capillary by means of the medium conduit means; and
    applying an electrical field in the at least one capillary to separate any samples present in the at least one capillary;
    wherein the injecting and applying steps are performed without breaking the sealed connections.

16. The method of claim 15, said at least one separation capillary having an outlet, said medium conduit means including medium inlet means and medium outlet means, and said connecting step sealingly connecting the outlet of said at least one separation capillary to medium inlet means and medium outlet means to form sealed connections between the outlet and viscous separation medium inlet and medium outlet means so that pressure greater than atmospheric pressure can be maintained in the at least one capillary;

wherein said injecting step injects viscous separation medium into the at least one capillary to purge the at least one capillary of old viscous separation medium, if any, in the at least one capillary by means of the medium inlet means.

17. The method of claim 15, further comprising repeating the injecting and applying steps without breaking the sealed connection.

18. The method of claim 15, wherein said connecting step forms sealed connections that can withstand over 400 psi.

* * * * *